United States Patent
Zi et al.

(10) Patent No.: US 9,126,990 B2
(45) Date of Patent: Sep. 8, 2015

(54) METHOD FOR SYNTHESIZING RIVAROXABAN INTERMEDIATE, 4-(4-[(5S)-(AMINOMETHYL)-2-OXO-1,3-OXAZOLIGDIN-3-YL]PHENYL) MORPHOLIN-3-ONE

(75) Inventors: Chunpeng Zi, Shanghai (CN); Luning Huang, Shanghai (CN); Jeannie Zhang, Shanghai (CN)

(73) Assignees: ZHEJIANG HUAHAI PHARMACEUTICAL CO., LTD, Zhejiang (CN); SHANGHAI SYNCORES TECHNOLOGIES, INC., Shanghai (CN)

( * ) Notice: Subject to any disclaimer, the term of this patent is extended or adjusted under 35 U.S.C. 154(b) by 38 days.

(21) Appl. No.: 14/126,361

(22) PCT Filed: Jan. 18, 2012

(86) PCT No.: PCT/CN2012/070530
§ 371 (c)(1),
(2), (4) Date: Dec. 13, 2013

(87) PCT Pub. No.: WO2012/171343
PCT Pub. Date: Dec. 20, 2012

(65) Prior Publication Data
US 2014/0114066 A1    Apr. 24, 2014

(30) Foreign Application Priority Data
Jun. 14, 2011   (CN) .......................... 2011 1 0158823

(51) Int. Cl.
*C07D 413/10*   (2006.01)
(52) U.S. Cl.
CPC .................. *C07D 413/10* (2013.01)

(58) Field of Classification Search
CPC .................................................. C07D 413/10
See application file for complete search history.

(56) References Cited

FOREIGN PATENT DOCUMENTS

| CN | 101415694 | | 4/2009 |
|---|---|---|---|
| CN | 102827154 | | 12/2012 |
| WO | 2005/068456 | * | 7/2005 |
| WO | 2009/002323 | * | 2/2009 |
| WO | WO 2010124385 | | 11/2010 |
| WO | 2011/012321 | * | 2/2011 |

OTHER PUBLICATIONS

Roehrig, Susanne "Discovery of the Novel Antithrombotic Agent 5-Chloro-N-({(5S)-2-oxo-3-[ 4-(3-oxomorpholin-4-yl)phenyl]-1,3-oxazolidin-5-yl}methyl)thiophene-2-carboxamide (BAY 59-7939): An Oral, Direct Factor Xa Inhibitor" J Med. Chem, 48:5900-5908 (2005).
Perrault, William "The Synthesis of N-Aryl-5(S)-aminomethyl-2-oxazolidinone Actibacterials and Derivatives in One Step from Aryl Carbamates" Organic Process Research & Development 7:533-546 (2003).
Mederski, Werner W. K. R. "A General Synthesis of 1-Aryl Carbamoyl-2-alkyl-4-aryl Substituted Semicarbazides as Nonbasic Factor Xa Inhibitors" Bioorganic & Medicinal Chemistry Letters 13:3715-3718 (2003).

* cited by examiner

*Primary Examiner* — Rebecca Anderson
(74) *Attorney, Agent, or Firm* — Norton Rose Fulbright US LLP

(57) ABSTRACT

The present invention discloses novel methods for synthesizing Rivaroxaban intermediate, i.e., 4-{4-[(5S)-5-(aminomethyl)-2-oxo-1,3-oxazolidin-3-yl]phenyl}morpholin-3-one. The novel methods provided in the present invention involve mild reaction conditions, convenient operations, easy purification, and low production costs, and thus the process is environmental-friendly and suitable for industrial production.

13 Claims, No Drawings

METHOD FOR SYNTHESIZING RIVAROXABAN INTERMEDIATE, 4-(4-[(5S)-(AMINOMETHYL)-2-OXO-1,3-OXAZOLIGDIN-3-YL]PHENYL) MORPHOLIN-3-ONE

This application is a national phase application under 35 U.S.C. §371 of International Application No. PCT/CN2012/070530 filed 18 Jan. 2012, which claims the priority of Chinese patent application No. 201110158823.3, filed on Jun. 14, 2011; The entire contents of the above-referenced applications are incorporated into the present application by reference.

TECHNICAL FIELD

The present invention relates to synthesis of pharmaceutical intermediate, more particularly to three novel methods for synthesizing an intermediate of anticoagulant Rivaroxaban, i.e., 4-{4-[(5S)-5-(aminomethyl)-2-oxo-1,3-oxazolidin-3-yl]phenyl}morpholin-3-one.

BACKGROUND ART

Rivaroxaban, having a chemical name of 5-chloro-N-({(5S)-2-oxo-3-[4-(3-oxo-4-morpholinyl)phenyl]-1,3-oxazolidin-5-yl}methyl-2-thiophenecarboxamide, has a structural formula (I) as follows:

Rivaroxaban is a novel highly selective anticoagulant developed by Bayer Company, Germany. Rivaroxaban was approved for marketing by the European Union in September 2008, and the brand name is Xarelto. Rivaroxaban can competitively inhibit the activity of free and bound factor Xa as well as prothrombin, prolong the prothrombin time (PT) and activated partial thromboplastin time (APTT) in a dose dependent mode, and can be used to prevent the formation of deep vein thrombosis (DVT) and pulmonary embolism (PE) in patients undergoing hip and knee replacement surgery.

The demand for Rivaroxaban will increase gradually along with its clinical application. WO 2005068456 disclosed a method for synthesizing Rivaroxaban, involving an important intermediate shown by formula 4, i.e., compound 4-{4-[(5S)-5-(aminomethyl)-2-oxo-1,3-oxazolidin-3-yl]phenyl}morpholin-3-one. The final product Rivaroxaban can be obtained by reacting the intermediate compound 4 with 5-chlorothiophene-2-carbonyl chloride in last step.

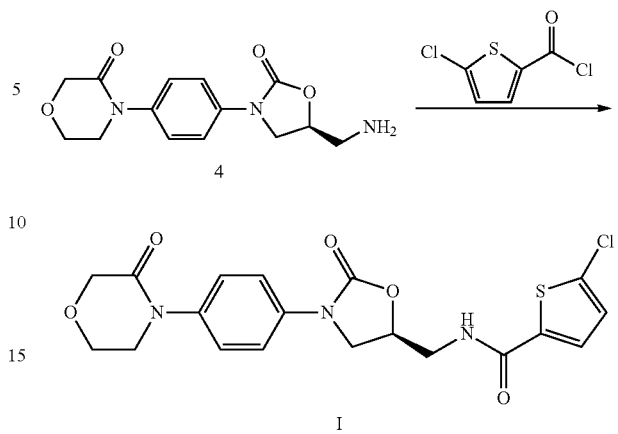

Compound 4 is an important intermediate for synthesizing Rivaroxaban. WO 0147919 also disclosed a method for preparing Rivaroxaban by using compounds 2-[(2S)-2-oxiranyl-methyl]-1-H-isoindole-1,3(2H)-dione and 4-(4-aminophenyl)-3-morpholinone as starting materials, in which the intermediate compound 4 is also involved, and the synthesis scheme is showed as follows:

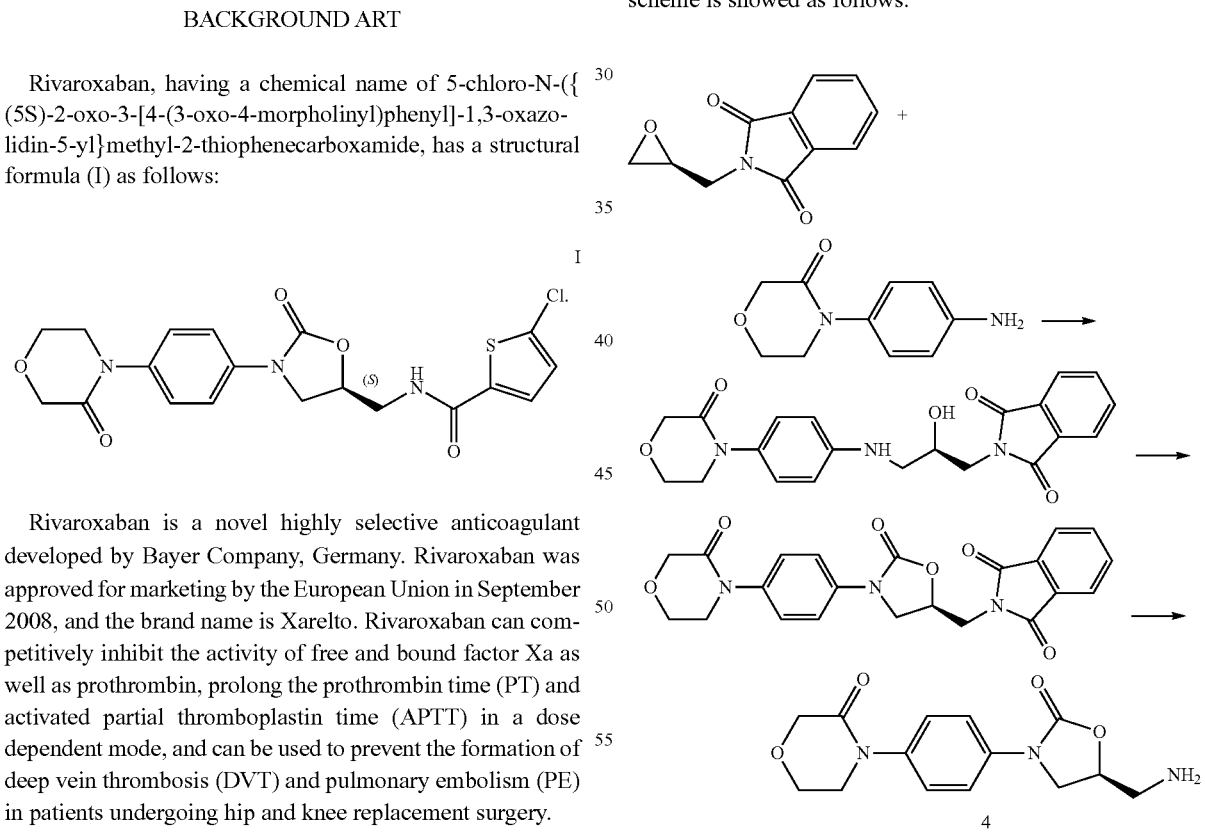

The major problems of this method are that:

1) the raw material 2-[(2S)-2-oxiranyl-methyl]-1-H-isoindole-1,3(2H)-dione is expensive; and the amino on oxazolidinone ring of Rivaroxaban is protected by phthalimide. Thus the removal of the protective group with methylamine increases the reaction steps and cost;

2) the reaction needs high temperature, long reaction time, high energy consumption, and high-cost, thus the process is not suitable for industrial production.

Therefore, the popularization and application of Rivaroxaban certainly will be promoted, if the preparation process of its intermediate compound 4 is optimized to decrease the price of drug substance.

SUMMARY OF THE INVENTION

An object of the present invention is to provide a novel method for synthesizing Rivaroxaban intermediate shown by structural formula 4, i.e. 4-{4-[(5S)-5-(aminomethyl)-2-oxo-1,3-oxazolidin-3-yl]phenyl}morpholin-3-one. The method is selected from the following three methods:

method I, comprising:

step (1): the condensation of compound 1 with compound 2 to form compound 3; and step (2): deprotecting compound 3 to provide compound 4, i.e., 4-{4-[(5S)-5-(aminomethyl)-2-oxo-1,3-oxazolidin-3-yl]phenyl}morpholin-3-one, wherein the synthesis scheme is described as follows:

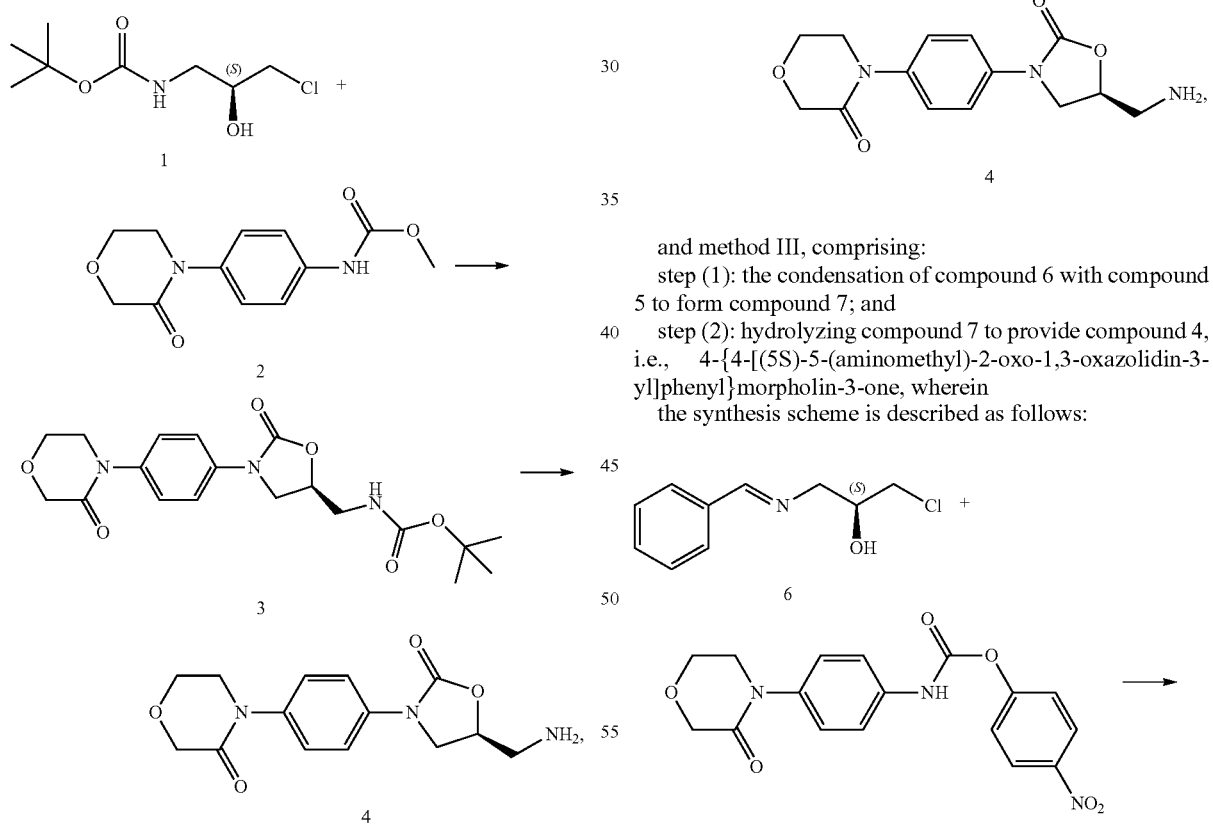

method II, comprising:

step (1): the condensation of compound 1 with compound 5 to form compound 3; and step (2): deprotecting compound 3 to provide compound 4, i.e., 4-{4-[(5S)-5-(aminomethyl)-2-oxo-1,3-oxazolidin-3-yl]phenyl}morpholin-3-one, wherein the synthesis scheme is described as follows:

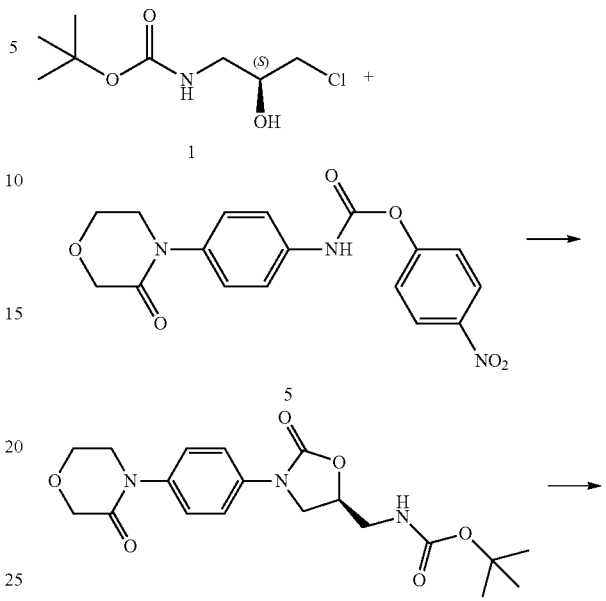

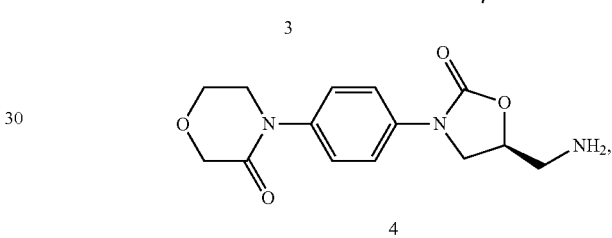

and method III, comprising:

step (1): the condensation of compound 6 with compound 5 to form compound 7; and step (2): hydrolyzing compound 7 to provide compound 4, i.e., 4-{4-[(5S)-5-(aminomethyl)-2-oxo-1,3-oxazolidin-3-yl]phenyl}morpholin-3-one, wherein the synthesis scheme is described as follows:

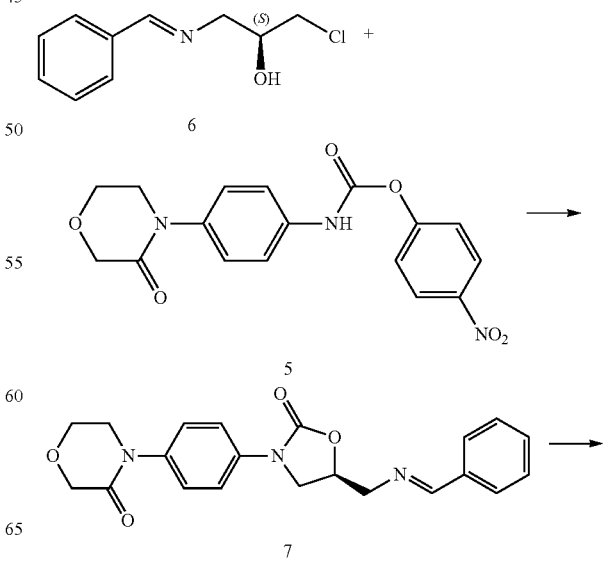

-continued

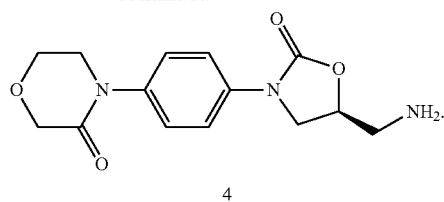
4

The novel method described in the embodiments of the present invention is selected from the following three methods:

method I, comprising:

step (1): the condensation of compound 1 with compound 2 in an inert solvent in the presence of lithium compound to provide compound 3; and step (2): deprotecting compound 3 in a reaction solvent under the action of hydrochloric acid or hydrogen chloride to provide compound 4, i.e., 4-{4-[(5S)-5-(aminomethyl)-2-oxo-1,3-oxazolidin-3-yl]phenyl}morpholin-3-one, wherein the synthesis scheme is described as follows:

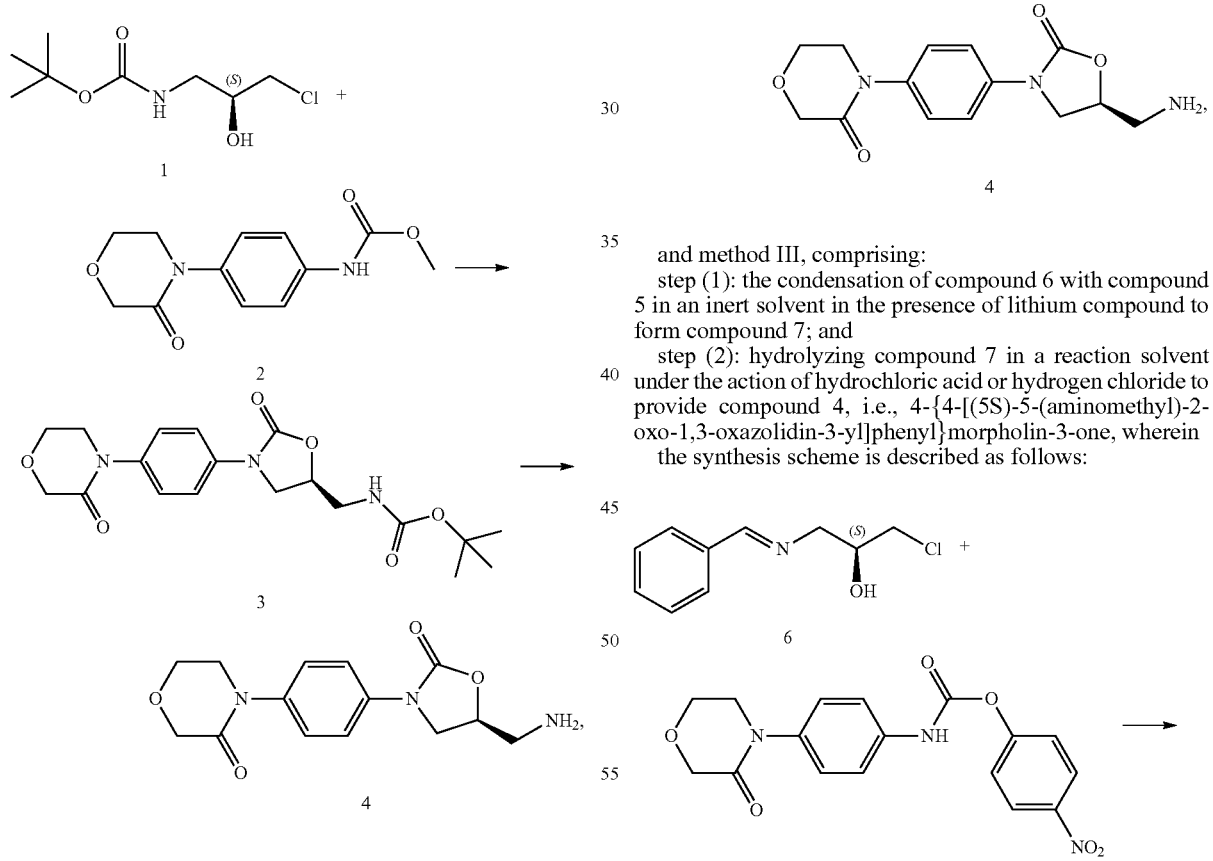

method II, comprising:

step (1): the condensation of compound 1 with compound 5 in an inert solvent in the presence of lithium compound to form compound 3; and step (2): deprotecting compound 3 in a reaction solvent under the action of hydrochloric acid or hydrogen chloride to provide compound 4, i.e., 4-{4-[(5S)-5-(aminomethyl)-2-oxo-1,3-oxazolidin-3-yl]phenyl}morpholin-3-one, wherein the synthesis scheme is described as follows:

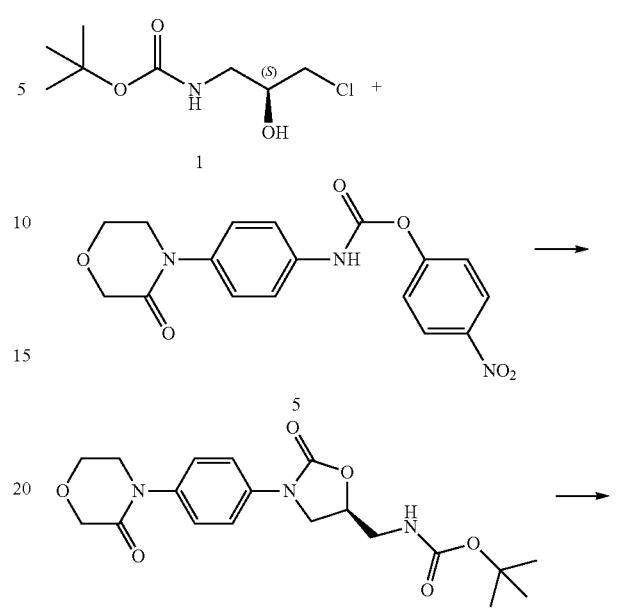

and method III, comprising:

step (1): the condensation of compound 6 with compound 5 in an inert solvent in the presence of lithium compound to form compound 7; and step (2): hydrolyzing compound 7 in a reaction solvent under the action of hydrochloric acid or hydrogen chloride to provide compound 4, i.e., 4-{4-[(5S)-5-(aminomethyl)-2-oxo-1,3-oxazolidin-3-yl]phenyl}morpholin-3-one, wherein the synthesis scheme is described as follows:

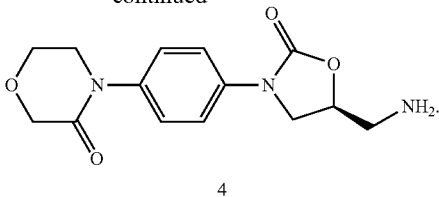

4

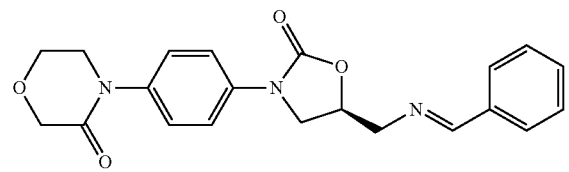

5

Regarding the above methods, the preparation methods of compound 1 and compound 6 are known in the prior art (See *Organic Process Research & Development,* 7(4):533-546, 2003). For the synthesis of compound 2, a novel method is described in WO 2010124385. For the synthesis of compound 5, a method is described in *Bioorganic & Medicinal Chemistry Letters* 13 (2003) 3715-3718.

In step (1) of the three methods mentioned in the present invention, the lithium compound is selected from the group consisting of lithium methoxide, lithium ethoxide, lithium isopropoxide or lithium tert-butoxide, and preferably lithium tert-butoxide.

The inert solvent is one or more selected from the group consisting of N,N-dimethylformamide, tetrahydrofuran, acetonitrile, dichloromethane, 1,4-dioxane and toluene, and preferably a mixed solvent of tetrahydrofuran and N,N-dimethylformamide.

The reaction temperature in step (1) is 0-30° C. Under different reaction conditions (comprising different lithium compounds and reaction solvents), a suitable reaction temperature can be chosen within this temperature range based on the criterion of the convenience of the control of reaction and the purification of product.

In step (2) of the three methods mentioned in the present invention, the employed reaction solvent is single or mixed solvent selected from the group consisting of alcohol, ketone, ether, halogenated alkane and water. The ether is tetrahydrofuran, dioxane, methyl tert-butyl ether or 1,2-dimethoxyethane. The alcohol is methanol, ethanol, propanol, isopropanol or butanol. The ketone is acetone, cyclohexanone or butanone. The halogenated alkane is dichloromethane or chloroform. The reaction solvent is preferably alcohol, particularly preferably ethanol. The reaction temperature is 0-100° C. For different reaction solvents, the temperature used can be chosen within the above range based on the principle that the reaction is completed in a reasonable time, the product is easily purified, and the yield is relatively high. The reaction temperature is preferably 20-30° C.

The present invention also provides new compound 3 and new compound 7 for preparing Rivaroxaban intermediate compound 4, i.e., 4-{4-[(5S)-5-(aminomethyl)-2-oxo-1,3-oxazolidin-3-yl]phenyl}morpholin-3-one, having the formulae as follows respectively:

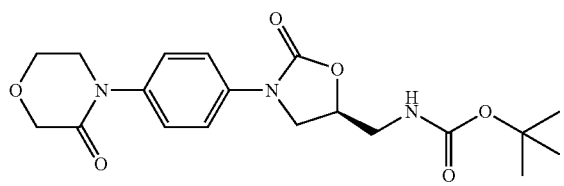

3

The novel methods for synthesizing Rivaroxaban intermediate compound 4, i.e., 4-{4-[(5S)-5-(aminomethyl)-2-oxo-1,3-oxazolidin-3-yl]phenyl}morpholin-3-one, provided in the present invention, involve mild reaction conditions, convenient operations, easy purification, and low production costs, and are environmental-friendly and suitable for industrial production.

DESCRIPTION OF EMBODIMENTS

For further understanding the present invention, the preferred embodiments are described below with reference to the examples. It should be understood that these descriptions are only for further illustrating the features and advantages of the present invention without limiting the claims of the present invention.

The effect of the present invention is described below with reference to the specific examples, but the protection scope of the present invention is not limited to the following examples.

The technical solutions of the present invention and the technical effects thereof will be further described below with reference to the examples, but the present invention is not thus limited to the scope of the examples.

Example 1

Preparation of Compound 3

8.35 g of compound 1 and 5.0 g of compound 2 were added to 30 ml of tetrahydrofuran. The temperature was decreased to 10° C. in ice bath. 6.4 g of lithium tert-butoxide was slowly added. The mixture was stirred at 20-30° C. for 24 hours. 100 ml of water and 100 ml of dichloromethane were added, and the layers separated after stirring. The organic layer was separated and concentrated to dryness. The residue dissolved in 20 ml of toluene by heating Cooled to 5-10° C. with stirring, some solid precipitated. The mixture was filtered to give 7.0 g of off-white solid. The yield was 90%.

$^1$H-NMR of compound 3: (400 MHz, $d_6$-DMSO) δ 1.36 (s, 9H), 3.27~3.30 (m, 2H), 3.70~3.72 (m, 2H), 3.82 (m, 1H), 3.97 (m, 2H), 4.12 (m, 1H), 4.19 (s, 2H), 4.7 (m, 1H), 7.40~7.58 (m, 4H) ppm.

Example 2

Preparation of Compound 3

25.0 g of compound 1 and 15.0 g of compound 2 were added to 30 ml of N,N-dimethylformamide and 50 ml of tetrahydrofuran. Cooled to 10° C. in ice bath, 20 g of lithium tert-butoxide was added slowly. The mixture was stirred at 20-30° C. for 24 hours. 300 ml of water and 300 ml of dichloromethane were added, and the layers separated after stirring. The organic layer was separated and concentrated to dryness. The residue dissolved in 40 ml of toluene by heating.

Cooled to 5-10° C. with stirring, some solid precipitated. The mixture was filtered to give 22.7 g of off-white solid. The yield was 97%.

Example 3

Preparation of Compound 3

1.7 g of compound 1 and 1.0 g of compound 2 were added to 2 ml of N,N-dimethylformamide and 4 ml of tetrahydrofuran. The mixture was cooled to 10° C. in ice bath. 0.7 g of lithium methoxide was slowly added. The reaction mixture was stirred at 20-30° C. for 24 hours. 20 ml of water and 20 ml of dichloromethane were added, and the layers separated after stirring. The organic layer was separated and concentrated to dry. The residue dissolved in 2 ml of toluene by heating. Cooled to 5-10° C. with stirring, some solid precipitated. The mixture was filtered to give 0.97 g of off-white solid. The yield was 62%.

Example 4

Preparation of Compound 3

8.35 g of compound 1 and 8.0 g of compound 5 were added to 30 ml of tetrahydrofuran. The mixture was cooled to 10° C. in ice bath. 6.4 g of lithium tert-butoxide was slowly added. The reaction mixture was stirred at 20-30° C. for 24 hours. 100 ml of water and 100 ml of dichloromethane were added, and the layers separated after stirring. The organic layer was separated and concentrated to dryness. The residue dissolved in 20 ml of toluene by heating. Cooled to 5-10° C. with stirring, some solid precipitated. The mixture was filtered to give 7.6 g of off-white solid. The yield was 87%.

Example 5

Preparation of Compound 3

25.0 g of compound 1 and 24.0 g of compound 5 were added to 30 ml of N,N-dimethylformamide and 50 ml of tetrahydrofuran. Cooled to 10° C. in ice bath., 20 g of lithium tert-butoxide was slowly added. The reaction mixture was stirred at 20-30° C. for 24 hours. 300 ml of water and 300 ml of dichloromethane were added, and the layers separated after stirring. The organic layer was separated and concentrated to dryness. The residue dissolved in 40 ml of toluene by heating. Cooled to 5-10° C. with stirring, some solid precipitated-. The mixture was filtered to give 24.2 g of off-white solid-. The yield was 92%.

Example 6

Preparation of Compound 7

8.35 g of compound 6 and 7.0 g of compound 5 were added to 30 ml of tetrahydrofuran. Cooled to 10° C. in ice bath, 6.4 g of lithium tert-butoxide was slowly added. The reaction mixture was stirred at 20-30° C. for 24 hours. 100 ml of water and 100 ml of dichloromethane were added, and the layers separated after stirring. The organic layer was separated and concentrated to dryness. The residue dissolved in 20 ml of toluene by heating. Cooled to 5-10° C. with stirring, some solid-precipitated The mixture was filtered to give 6.3 g of off-white solid. The yield was 85%.

Compound 7 is identified as follows: $^1$H-NMR (400 MHz, $CDCl_3$) δ 3.31~3.42 (m, 2H), 3.57~3.62 (m, 2H), 3.76 (m, 1H), 3.89 (m, 2H), 3.99 (m, 1H), 4.10 (s, 2H), 4.9 (m, 1H), 6.80~7.68 (m, 9H), 8.40 (s, 1H) ppm.

Example 7

Preparation of Compound 7

25.0 g of compound 6 and 21.0 g of compound 5 were added to 30 ml of N,N-dimethylformamide and 50 ml of tetrahydrofuran. Cooled to 10° C. in ice bath, 20 g of lithium tert-butoxide was slowly added. The reaction mixture was stirred at 20-30° C. for 24 hours. 300 ml of water and 300 ml of dichloromethane were added, and the layers separated after stirring. The organic layer was separated and concentrated to dryness. The residue dissolved in 40 ml of toluene by heating. Cooled to 5-10° C. with stirring, some solid precipitated. The mixture was filtered to give 20.5 g of off-white solid. The yield was 92%.

Example 8

Preparation of Compound 4

5.0 g of compound 3 was added to 50 ml of ethanol. 10 ml of 37% (w/w) hydrochloric acid was added with stirring. The reaction mixture was stirred at room temperature for 24 hours. After vacuum filtration, the filter cake was washed with 10 ml of ethanol, and 3.8 g of off-white solid was obtained as product. The yield was 90%.

Example 9

Preparation of Compound 4

5.0 g of compound 3 was added to 50 ml of dioxane. 10 ml of 37% (w/w) hydrochloric acid was added with stirring. The reaction mixture was stirred at room temperature for 24 hours. After vacuum filtration, the filter cake was washed with 10 ml of ethanol, and 3.27 g of off-white solid was obtained as product. The yield was 78%.

Example 10

Preparation of Compound 4

5.0 g of compound 3 was added to 50 ml of acetone. 10 ml of 37% (w/w) hydrochloric acid was added with stirring. The reaction mixture was stirred at room temperature for 24 hours. After vacuum filtration, the filter cake was washed with 10 ml of acetone, and 3.1 g of off-white solid was obtained as product. The yield was 73%.

Example 11

Preparation of Compound 4

5.0 g of compound 3 was added to 20 ml of water. 10 ml of 37% (w/w) hydrochloric acid was added with stirring. The reaction mixture was conducted at room temperature for 36 hours. The reaction mixture was concentrated to remove water under reduced pressure at 60° C. After addition of 10 ml of acetone, the mixture was stirred for 10 minutes. Then the mixture was filtered to give 3.2 g of off-white solid. The yield was 75.8%.

Example 12

Preparation of Compound 4

5.0 g of compound 3 was added to 50 ml of dichloromethane. 10 ml of 37% (w/w) hydrochloric acid was added with stirring. The reaction mixture was stirred at room temperature for 24 hours. Dichloromethane and water were removed under reduced pressure. After addition of 10 ml of acetone, the mixture was stirred for 10 minutes. The mixture was filtered to give 2.9 g of off-white solid. The yield was 68.7%.

Example 13

Preparation of Compound 4

5.0 g of compound 7 was added to 50 ml of ethanol. 10 ml of 37% (w/w) hydrochloric acid was added with stirring. The reaction mixture was stirred at room temperature for 24 hours. After vacuum filtration, the filter cake was washed with 10 ml of ethanol, and 3.88 g of off-white solid was obtained as product. The yield was 90%.

Example 14

Preparation of Compound 4

5.0 g of compound 7 was added to 50 ml of acetone. 10 ml of 37% (w/w) hydrochloric acid was added with stirring. The reaction mixture was stirred at room temperature for 24 hours. After vacuum filtration, the filter cake was washed with 10 ml of acetone, and 3.2 g of off-white solid was obtained as product. The yield was 75%.

Example 15

Preparation of Compound 4

5.0 g of compound 7 was added to 20 ml of water. 10 ml of 37% (v/v) hydrochloric acid was added with stirring. The reaction mixture was stirred at room temperature for 36 hours. The reaction mixture was concentrated to remove water under reduced pressure at 60° C. After addition of 10 ml of acetone, the mixture was stirred for 10 minutes. Then the mixture was filtered to give 3.3 g of off-white solid. The yield was 75.8%.

In each example of the specific embodiments in the present invention, structure of compound 3 and compound 7 are identified, and the identification data are recorded in example 1 and example 6 respectively.

The novel methods for synthesizing Rivaroxaban intermediate, 4-{4-[(5S)-5-(aminomethyl)-2-oxo-1,3-oxazolidin-3-yl]phenyl}morpholin-3-one proposed in the present invention are described through the examples. practitioners skilled in the related art obviously can modify or change and combine the novel methods for synthesizing Rivaroxaban intermediate, 4-{4-[(5S)-5-(aminomethyl)-2-oxo-1,3-oxazolidin-3-yl]phenyl}morpholin-3-one described herein without departing from the contents, spirit and scope of the present invention, so as to achieve the present invention. It should be particularly noted that all similar replacements and modifications are apparent for practitioners skilled in the art, and are considered to be within in the spirit, scope and contents of the present invention.

The invention claimed is:

1. A method for synthesizing Rivaroxaban intermediate, 4-{4-[(5S)-5-(aminomethyl)-2-oxo-1,3-oxazolidin-3-yl]phenyl}morpholin-3-one, selected from the following three methods:

method I, comprising:
  step (1): the condensation of compound 1 with compound 2 to form compound 3; and
  step (2): deprotecting compound 3 to provide compound 4, i.e., 4-{4-[(5S)-5-(aminomethyl)-2-oxo-1,3-oxazolidin-3-yl]phenyl}morpholin-3-one, wherein the reaction scheme is described as follows:

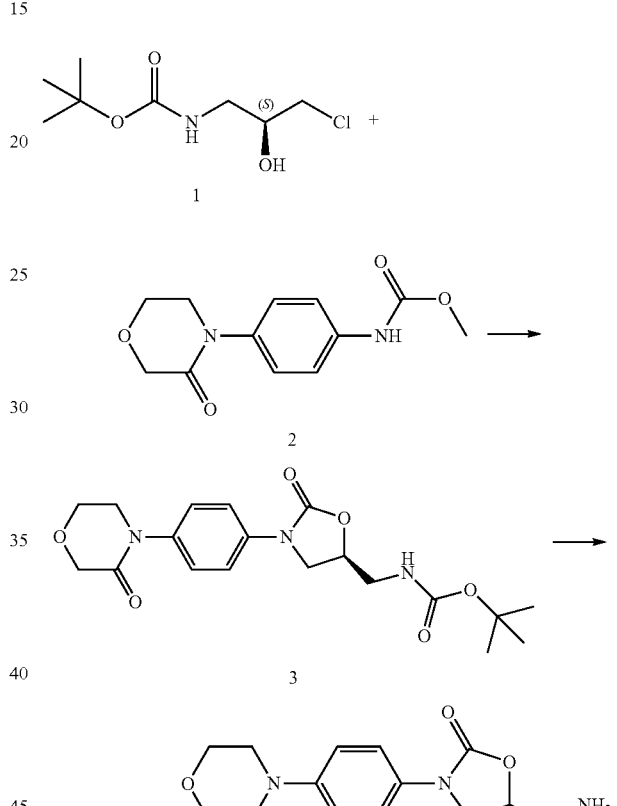

method II, comprising:
  step (1): the condensation of compound 1 with compound 5 to form compound 3;
  step (2): deprotecting compound 3 to provide compound 4, i.e., 4-{4-[(5S)-5-(aminomethyl)-2-oxo-1,3-oxazolidin-3-yl]phenyl}morpholin-3-one, wherein the reaction scheme is described as follows:

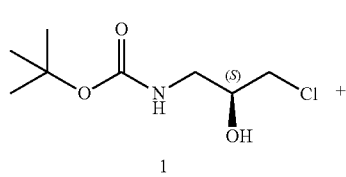

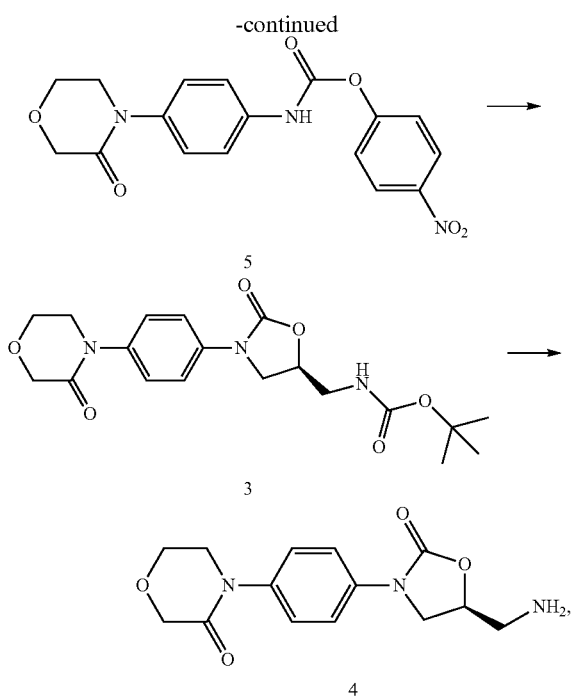

and method III, comprising:
  step (1): the condensation of compound 6 with compound 5 to form compound 7; and
  step (2): hydrolyzing compound 7 to provide compound 4, i.e., 4-{4-[(5S)-5-(aminomethyl)-2-oxo-1,3-oxazolidin-3-yl]phenyl}morpholin-3-one, wherein the reaction scheme is described as follows:

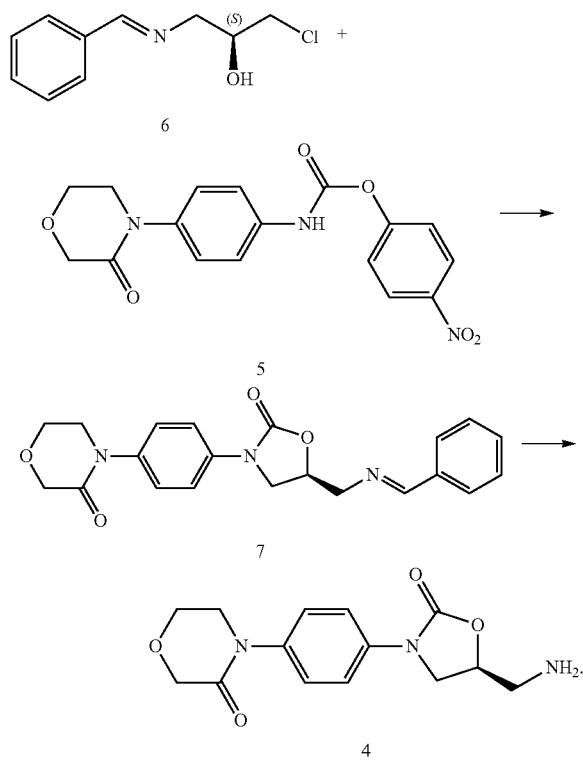

2. The method for synthesizing Rivaroxaban intermediate, 4-{4-[(5S)-5-(aminomethyl)-2-oxo-1,3-oxazolidin-3-yl]phenyl}morpholin-3-one according to claim 1, characterized in that, the method is selected from the following three methods:
  method I, comprising:
    step (1): the condensation of compound 1 with compound 2 in an inert solvent in the presence of lithium compound to form compound 3; and
    step (2): deprotecting compound 3 in a reaction solvent in the presence of hydrochloric acid or hydrogen chloride to provide compound 4, i.e., 4-{4-[(5S)-5-(aminomethyl)-2-oxo-1,3-oxazolidin-3-yl]phenyl}morpholin-3-one;
  method II, comprising:
    step (1): the condensation of compound 1 with compound 5 in an inert solvent in the presence of lithium compound to form compound 3; and
    step (2): deprotecting compound 3 in an reaction solvent under the action of hydrochloric acid or hydrogen chloride to provide compound 4, i.e., 4-{4-[(5S)-5-(aminomethyl)-2-oxo-1,3-oxazolidin-3-yl]phenyl}morpholin-3-one;
  method III, comprising:
    step (1): the condensation of compound 6 with compound 5 in an inert solvent in the presence of lithium compound to form compound 7;
    step (2): hydrolyzing compound 7 in a reaction solvent in the presence of hydrochloric acid or hydrogen chloride to provide compound 4, i.e., 4-{4-[(5S)-5-(aminomethyl)-2-oxo-1,3-oxazolidin-3-yl]phenyl}morpholin-3-one.

3. The method for synthesizing Rivaroxaban intermediate, 4-{4-[(5S)-5-(aminomethyl)-2-oxo-1,3-oxazolidin-3-yl]phenyl}morpholin-3-one according to claim 2, characterized in that, the lithium compound in step (1) of the three methods is one lithium compound selected from the group consisting of lithium methoxide, lithium ethoxide, lithium isopropoxide and lithium tert-butoxide, and preferably lithium tert-butoxide.

4. The method for synthesizing Rivaroxaban intermediate, 4-{4-[(5S)-5-(aminomethyl)-2-oxo-1,3-oxazolidin-3-yl]phenyl}morpholin-3-one according to claim 2, characterized in that, the inert solvent in step (1) of the three methods is one or more selected from the group consisting of N,N-dimethylformamide, tetrahydrofuran, acetonitrile, dichloromethane, 1,4-dioxane and toluene, and preferably a mixed solvent of tetrahydrofuran and N,N-dimethylformamide.

5. The method for synthesizing Rivaroxaban intermediate, 4-{4-[(5S)-5-(aminomethyl)-2-oxo-1,3-oxazolidin-3-yl]phenyl}morpholin-3-one according to claim 2, characterized in that, the reaction temperature in step (1) of the three methods is 0-30° C.

6. The method for synthesizing Rivaroxaban intermediate, 4-{4-[(5S)-5-(aminomethyl)-2-oxo-1,3-oxazolidin-3-yl]phenyl}morpholin-3-one according to claim 2, characterized in that, the reaction solvent in step (2) of the three methods is one or more selected from the group consisting of alcohol, ketone, ether, halogenated alkane and water.

7. The method for synthesizing Rivaroxaban intermediate, 4-{4-[(5S)-5-(aminomethyl)-2-oxo-1,3-oxazolidin-3-yl]phenyl}morpholin-3-one according to claim 2, characterized in that, the ether is tetrahydrofuran, dioxane, methyl tert-butyl ether or 1,2-dimethoxyethane; the alcohol is methanol, ethanol, propanol, isopropanol or butanol; the ketone is acetone, cyclohexanone or butanone; and the halogenated alkane is dichloromethane or chloroform.

8. The method for synthesizing Rivaroxaban intermediate, 4-{4-[(5S)-5-(aminomethyl)-2-oxo-1,3-oxazolidin-3-yl]phenyl}morpholin-3-one according to claim 2, characterized in that, the reaction temperature in step (2) of the three methods is 0-100° C., and preferably 20-30° C.

9. Compound 3 for preparing Rivaroxaban intermediate, 4-{4-[(5S)-5-(aminomethyl)-2-oxo-1,3-oxazolidin-3-yl]phenyl}morpholin-3-one, having the chemical formula as follows:

3

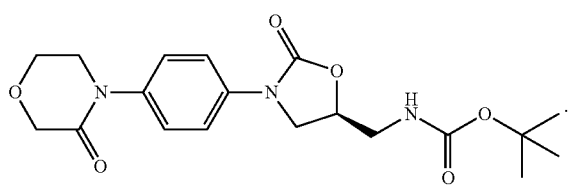

10. Compound 7 for preparing Rivaroxaban intermediate, 4-{4-[(5S)-5-(aminomethyl)-2-oxo-1,3-oxazolidin-3-yl]phenyl}morpholin-3-one, having the chemical formula as follows:

7

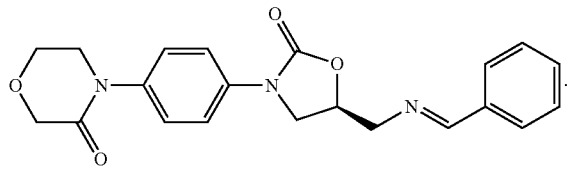

11. The method for synthesizing Rivaroxaban intermediate, 4-{4-[(5S)-5-(aminomethyl)-2-oxo-1,3-oxazolidin-3-yl]phenyl}morpholin-3-one according to claim 3, characterized in that, the reaction temperature in step (1) of the three methods is 0-30° C.

12. The method for synthesizing Rivaroxaban intermediate, 4-{4-[(5S)-5-(aminomethyl)-2-oxo-1,3-oxazolidin-3-yl]phenyl}morpholin-3-one according to claim 4, characterized in that, the reaction temperature in step (1) of the three methods is 0-30° C.

13. The method for synthesizing Rivaroxaban intermediate, 4-{4-[(5S)-5-(aminomethyl)-2-oxo-1,3-oxazolidin-3-yl]phenyl}morpholin-3-one according to claim 6, characterized in that, the reaction temperature in step (2) of the three methods is 0-100° C., and preferably 20-30° C.

\* \* \* \* \*

UNITED STATES PATENT AND TRADEMARK OFFICE
CERTIFICATE OF CORRECTION

PATENT NO. : 9,126,990 B2  
APPLICATION NO. : 14/126361  
DATED : September 8, 2015  
INVENTOR(S) : Chunpeng Zi et al.

Page 1 of 1

It is certified that error appears in the above-identified patent and that said Letters Patent is hereby corrected as shown below:

On the Title Page, Item (54) and in the Specification, Column 1, lines 3-4, delete "4-{4-[(5S)-(AMINOMETHYL)-2-OXO-1,3-OXAZOLIGDIN-3-YL]PHENYL}" and insert --4-{4-[(5S)-5-(AMINOMETHYL)-2-OXO-1,3-OXAZOLIDIN-3-YL]PHENYL}-- therefor.

Signed and Sealed this  
Twenty-sixth Day of April, 2016

Michelle K. Lee  
*Director of the United States Patent and Trademark Office*